United States Patent [19]

Cosmescu

[11] Patent Number: 5,312,397
[45] Date of Patent: May 17, 1994

[54] LENS EXCHANGER FOR A SURGICAL LASER SYSTEM AND METHOD THEREFOR

[76] Inventor: Ioan Cosmescu, 14449 N. 22nd St., Phoenix, Ariz. 85022

[21] Appl. No.: 763,562

[22] Filed: Sep. 23, 1991

Related U.S. Application Data

[63] Continuation-in-part of Ser. No. 448,329, Dec. 11, 1989, Pat. No. 5,114,422, and Ser. No. 527,140, May 22, 1990, Pat. No. 5,066,294.

[51] Int. Cl.$^5$ .............................................. A61B 17/36
[52] U.S. Cl. .......................................... 606/14; 606/2; 606/17
[58] Field of Search ..................................... 606/10–14, 606/17–19, 2–6; 128/4, 6, 395, 396, 397; 359/813, 821, 827, 703

[56] References Cited

U.S. PATENT DOCUMENTS

| | | | |
|---|---|---|---|
| 3,720,213 | 3/1973 | Hobart et al. | 606/4 |
| 4,473,074 | 9/1984 | Vassiliadis | 606/10 |
| 4,503,854 | 3/1985 | Jako | 606/11 |
| 4,576,160 | 3/1986 | Tanaka | 606/10 |
| 4,597,380 | 7/1986 | Raif et al. | 606/18 |
| 4,718,422 | 1/1988 | Rosenberg | 606/17 |

Primary Examiner—Stephen C. Pellegrino
Assistant Examiner—M. Peffley
Attorney, Agent, or Firm—Harry M. Weiss

[57] ABSTRACT

A lens exchanger for a laser surgical tool is disclosed. This lens exchanger installs easily between the coupler for the laser source and the surgical tool (such as a laparoscope). The lens exchanger protects the lens on the surgical tool from contamination by water vapor, smoke and debris. The lens exchanger can be configured to provide clear windows so the surgeon can conveniently switch to a clean lens during surgery as needed. The lens exchanger can also be configured with lenses that change the focus of the laser cutting beam, making the cutting spot more or less focused as required by the particular application.

21 Claims, 2 Drawing Sheets

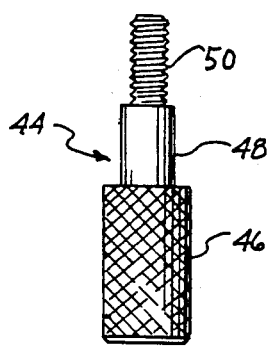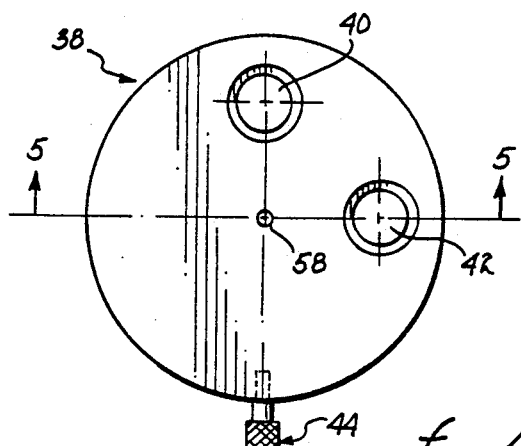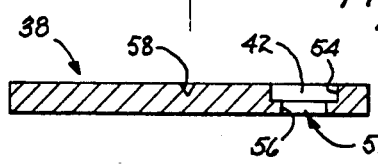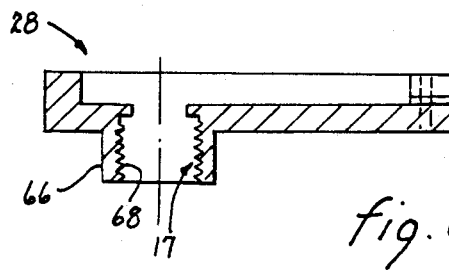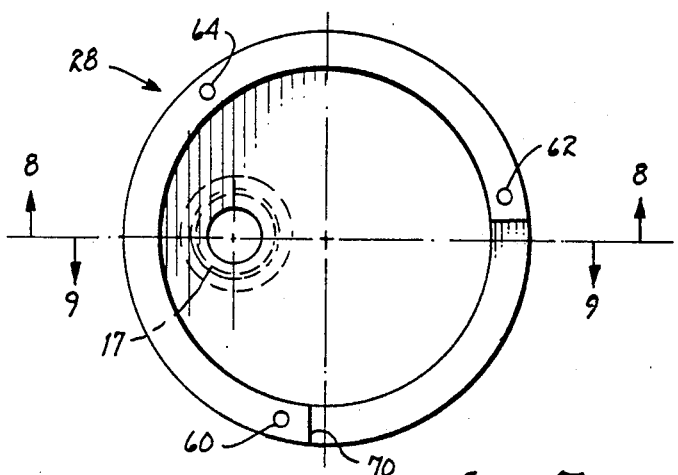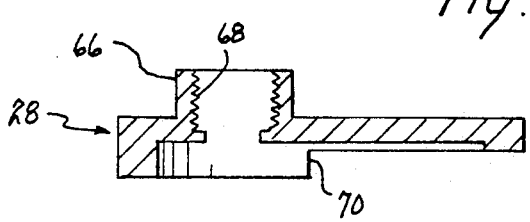

LENS EXCHANGER FOR A SURGICAL LASER SYSTEM AND METHOD THEREFOR

RELATED APPLICATION

This patent application is a continuation-in-part of my earlier patent application entitled "LASER LAPAROSCOPE ASSEMBLY AND METHOD THEREFOR", Ser. No. 07/448,329, now U.S. Pat. No. 5,114,422, filed Dec. 11, 1989, and is also a continuation-in-part of my earlier patent application entitled "PERFORMANCE TESTER APPARATUS FOR A SURGICAL LASER SYSTEM AND METHOD THEREFOR", Ser. No. 07/B27,140, filed May 22, 1990, now U.S. Pat. No. 5,066,294. These pending patent applications are incorporated herein by reference thereto.

FIELD OF THE INVENTION

This invention generally relates to surgical laser systems and methods therefor, and more specifically relates to a surgical laser system and method therefor having a lens exchanger through which the laser beam passes.

DESCRIPTION OF THE PRIOR ART

Generally, a surgical laser system utilizes two laser beams. One laser beam is a visible aiming beam typically provided by a relatively low energy Helium-Neon (HeNe) gas laser. The second laser beam is an invisible cutting beam typically provided by a relatively high energy Carbon Dioxide ($CO_2$) gas laser. These two laser beams are narrowly confined within an articulated arm assembly on a laser surgical tool. A handpiece attached to the end of the arm assembly is manipulated by the surgeon during a laser type surgical operation to focus or to aim the laser cutting beam at the proper location within the field of the surgical operation.

Since the laser cutting beam is normally invisible to the human eye, a second laser beam which is within the visible spectrum is used as an aiming beam. The aiming beam indicates to the surgeon the exact position where the cutting beam will cut with a visible dot on the tissue of the surgical patient When the surgeon has positioned the aiming beam at the desired focus or location, the surgeon then depresses a foot switch associated with the laser surgical system to effectively remove the visible laser aiming beam and activate the laser cutting beam thereby making an incision for the laser surgical operation.

The cutting beam can produce smoke and water vapor while cutting tissue, which can deposit on the lens of the laser surgical tool. The smoke and water vapor on the lens can absorb and diverge the cutting beam, reducing the laser power at the cutting point, and causing a wider spot than would be produced with a clean lens. The prior art laser surgical tools have fixed, non-removable lenses. When contamination of the lens occurs, the surgeon must either switch to a clean laser surgical tool, stop and clean the laser surgical tool currently in use, or continue the surgery with reduced performance of the laser surgical tool. If the surgeon stops the procedure to switch to a clean laser surgical tool or to clean the laser surgical tool currently in use, precious time is lost and great inconvenience results. Continuing the surgery with a laser surgical tool that delivers reduced performance could jeopardize the accuracy and exactness required by many surgical procedures. These problems could be avoided by providing a means to conveniently switch from a contaminated lens to a clean lens during surgery.

During some surgical procedures it is desirable to change the width of the cutting laser spot at the cutting site. This could be accomplished by changing the lens on the laser surgery tool. The prior art laser surgery systems have fixed, non-removable lenses, and offer no convenient means of changing to a different lens during surgery in order to change the width of the cutting beam.

Therefore, there existed a need to provide a laser surgical system with a lens exchanger that allows the surgeon to conveniently change lenses during a surgical procedure. This lens exchanger provides two separate lenses to allow changing from one lens to the other lens during a surgical procedure. The lens exchanger provides a way to replace a lens that may be blurred with water and smoke during surgery with a clean lens so surgery may continue without delay or inconvenience. The lens exchanger also provides a way to give two varying widths of laser beam spots at the cutting site, allowing greater flexibility during surgery.

SUMMARY OF THE INVENTION

It is an object of this invention to provide a lens exchanger and method for a laser surgical tool that provides multiple lenses that can be easily changed during surgery.

It is a further object of this invention to provide a lens exchanger and method for a laser surgical tool that provides multiple lenses of identical optical characteristics to allow changing from a contaminated lens to a clean lens during surgery.

It is a still further object of this invention to provide a lens exchanger and method for a laser surgical tool that provides multiple lenses of differing optical characteristics to allow changing the lens during surgery and thereby changing the width of the laser beam spot at the cutting point It is another object of this invention to provide a lens exchanger and method for a laser laparoscope According to the present invention, a laser surgical tool and method are provided This tool is coupled to a lens exchanger of the present invention which allows the surgeon to change the lens on the laser surgical tool as needed during surgery. The surgeon may need to change lenses due to a lens becoming blurred by smoke, water vapor and debris. Alternatively, the surgeon may need to change lenses to provide a cutting spot of a different width during the surgery.

With the lens exchanger installed on the laser surgical tool, the original lens on the laser surgical tool is protected from contamination and damage by the additional lens provided in the lens exchanger.

The foregoing and other objects, features and advantages will be apparent from the following description of the preferred embodiment of the invention as illustrated in the accompanying drawings.

BRIEF DESCRIPTION OF THE DRAWINGS

FIG. 4 is a top view of the lens plate for the lens exchanger shown in FIG. 1.

FIG. 5 is a cross sectional view of the lens plate of FIG. 4 taken along the line 5—5.

FIG. 6 is a side view of the thumbscrew used on the lens plate of FIG. 4.

FIG. 7 is a bottom view of the bottom housing for the lens exchanger shown in FIG. 1.

FIG. 8 is a cross sectional view of the bottom housing of FIG. 7 taken along the line 8—8.

FIG. 9 is a cross sectional view of the bottom housing of FIG. 7 taken along the line 9—9.

DESCRIPTION

Figure 1:
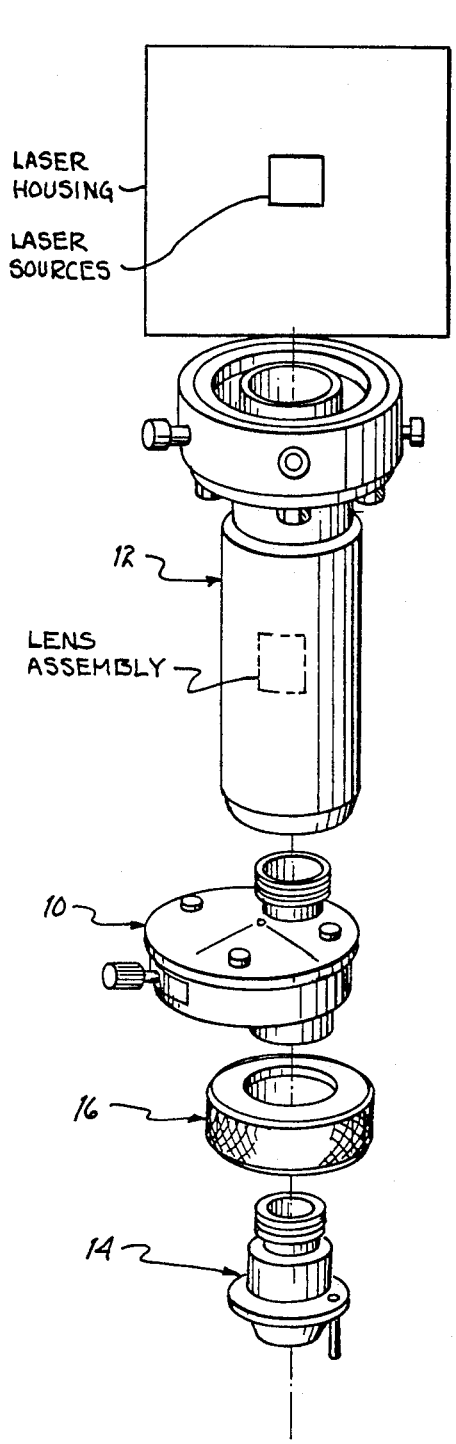
FIG. 1 is a perspective view of the lens exchanger of the present invention as used with a laser laparoscope.

The lens exchanger of the present invention can be used with a variety of different laser surgical tools. The description contained herein is limited for illustrative purposes to the specific case of one particular configuration of the lens exchanger which is used with a laser laparoscope. This disclosure is for illustrative purposes only, and does not limit the scope of the present invention to that specific example described herein and illustrated in the drawings.

Referring to the figures, FIG. 1 shows the lens exchanger 10 of the present invention as it is used with a laser laparoscope. The laser laparoscope has a laser source (not shown) which couples to the top portion of coupler 12 in FIG. 1. In the prior art laser laparoscope surgical tool, coupler 12 is coupled to the laparoscope 14 through ring member 16. As can be seen from FIG. 1, the lens exchanger 10 is installed between the coupler 12 and the laparoscope 14.

The coupler 12 includes a lens assembly (not shown) to appropriately focus both the aiming beam and the cutting beam. In the prior art laser laparoscope surgical tool the lens assembly inside coupler 12 is subject to contamination by water vapor, smoke and debris during a surgical procedure. With the lens exchanger 10 installed, the lens assembly inside coupler 12 is completely protected from contamination, since the lens exchanger 10 separates the lens assembly in coupler 12 from the laparoscope 14.

Figure 3:
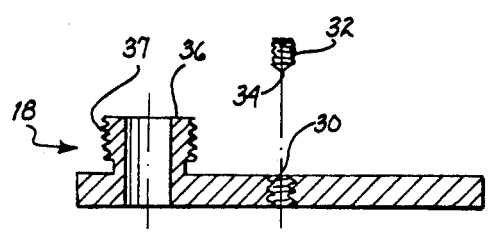
FIG. 3 is a cross sectional view of the top housing shown in FIG. 2 taken along the line 3—3.
Figure 2:
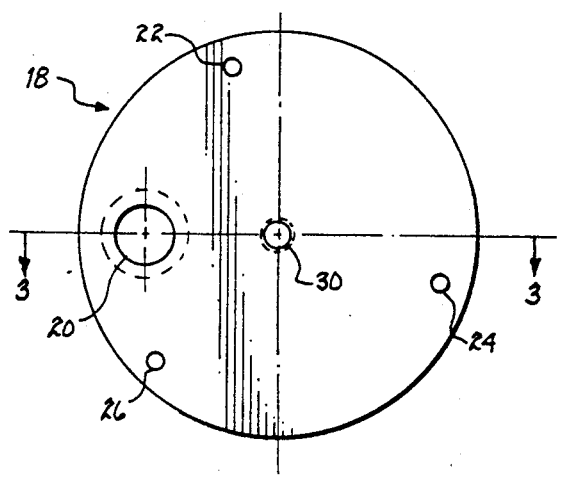
FIG. 2 is a top view of the top housing for the lens exchanger shown in FIG. 1.

FIG. 2 shows the top housing 18 of lens exchanger 10. This top housing 18 includes a hole 20 eccentricly located through which the laser beams pass, and three mounting holes 22, 24, and 26. Top housing 18 has a threaded hole 30 at the center. As shown in FIG. 3, a set screw 32 with a conical tip 34 is installed in threaded hole 30. Top housing 18 has an extended portion 36 as shown with external threads 37 for coupling the top housing of lens exchanger 10 to coupler 12.

FIG. 4 shows the lens plate 38 wherein are mounted two lenses 40 and 42. Lens plate 38 has a thumb screw 44 installed on one edge as shown. Thumb screw 44 is shown in more detail in FIG. 6, and includes a knurled portion 46, a spacer portion 48, and a threaded portion 50. Threaded portion 50 of thumb screw 44 is screwed into a tapped hole in the edge of lens plate 38, as shown in FIG. 4.

The cross sectional view of the lens plate 38 is shown in FIG. 5. The lens recess 52 has an upper portion 54 of one diameter and a lower portion 56 of a smaller diameter for positive retention of the lens 42 once it is properly installed in lens recess 52. Lens plate 38 also has a conical recess 58. When the lens plate 38 is properly installed in the lens exchanger 10, set screw 32 is screwed in until the conical tip 34 of set screw 32 presses into the conical recess 58 of lens plate 38, thereby aligning the lens plate 38 to the proper position.

The bottom housing 28 of lens exchanger 10 is shown in FIGS. 7, 8, and 9. Bottom housing 28 has three mounting holes 60, 62, and 64 as shown in FIG. 7, which correspond to mounting holes 22, 24, and 26, respectively, on top housing 18 (FIG. 2). Mounting holes 60, 62, and 64 are typically tapped holes. As shown in FIG. 8, bottom housing 28 has an extended portion 66 with internal threads 68 for engaging the laparoscope 14. The depth of bottom housing 28 is such that the lens plate 38 fits into bottom housing 28. As shown in FIG. 9, bottom housing 28 has a cutout portion 70 which allows thumb screw 44 to pass through bottom housing 28, and which allows 90 degree rotation of the lens plate 18 by pushing on the thumb screw 44.

The lens exchanger 10 is assembled in the following steps:

1) Install lenses in lens plate 38.
2) Install thumb screw 44 in lens plate 38.
3) Set lens plate 38 into bottom housing 28.
4) Put top housing 18 over lens plate 38 and bottom housing 28
5) Install three screws through top housing 18 into the tapped holes provided in bottom housing 28.
6) Install set screw 32 and tighten until snug, allowing the lens plate 38 to rotate.

OPERATION

As shown in FIG. 1, the lens exchanger 10 is used in conjunction with a laser (not shown), a coupler 12, a ring member 16, and a laparoscope 14. With these components all correctly coupled together, the laser laparoscope is ready for use. In one configuration, the lens exchanger is configured with two clear windows that do not change the focus of the laser dot at the tissue. This type of lens exchanger would allow a surgeon to switch to the second lens during surgery when the first lens becomes contaminated with water vapor, smoke, or debris. A second type of lens exchanger would provide one clear window which does not change the focus of the laser dot, and a second lens that changes the focus of the laser dot. This would allow the surgeon to switch from the standard dot focus provided on coupler 12 to a secondary dot focus provided by the second lens during surgery. A third type of lens exchanger would provide two lenses that change the focus of the laser dot. This allows the surgeon to configure the laser surgical tool to two specific dot sizes the surgeon specifies, allowing for custom configuration of the laser surgical tool.

The surgeon begins usage of the lens exchanger 10 with the thumb screw 44 pushed completely in one direction until it contacts the housing and cannot move further. In this position, one of the lenses is correctly aligned for use. To change lenses, the surgeon pushes the thumb screw 44 in the only direction it can move, which causes a rotation of the lens plate 38. The surgeon continues pushing the thumb screw 44 until it contacts the housing of lens exchanger 10, stopping rotation of the lens plate 90 degrees from the original position. At this position a second lens is correctly positioned within the lens exchanger 10 and ready for use.

While the invention has been described in its preferred embodiment, it is to be understood that the words which have been used are words of description rather than limitation, and that changes may be made within the purview of the appended claims without departing from the true scope and spirit of the invention in its broader aspects. For example, the lens plate could contain more than two lenses, providing the surgeon with several different lenses to provide greatest flexibility and convenience during surgery.

I claim:

1. A laser surgical system comprising, in combination:
    a laser housing;
    laser cutting means consisting of a single laser cutting beam for cutting tissue during surgery enclosed in said laser housing;
    laser aiming means coupled to said laser cutting means for aiming said laser cutting means and enclosed in said laser housing with said laser cutting means;
    coupler means having a fixed lens assembly located therein and coupled to said laser housing to position and focus said laser cutting means and said laser aiming means;
    lens exchanger apparatus means comprises a single rotatable plate coupled to said coupler means for selectively rotating at least one of at least two lenses in said coupler means, said at least two lenses being removably coupled to said single rotatable plate; and
    surgical tool means coupled to said lens exchanger apparatus means.

2. The system of claim 1 wherein said laser cutting means comprising an invisible, relatively high power Carbon Dioxide ($CO_2$) laser.

3. The system of claim 1 wherein said laser aiming means comprising a visible, relatively low power Helium Neon (HeNe) laser.

4. The system of claim 1 wherein said coupler means comprising connection means which couples said laser housing to said coupler means, and lens assembly means for focusing the laser output of said laser cutting means and said laser aiming means.

5. The system of claim 1 wherein said lens exchanger apparatus means comprises, in combination:
    an upper housing having a laser passage and an adapter coupling assembly;
    a lower housing having a laser passage coincident to said laser passage of said upper housing, said lower housing being fixedly coupled to said upper housing;
    lens plate means located within said lower housing providing multiple lenses, one of which aligns with said laser passage in said upper housing and with said laser passage in said lower housing in a first lens position;
    lens exchanging means for moving the position of said one of said multiple lenses from said first lens position to a second lens position to align a different lens of said multiple lenses with said laser passage of said upper housing and with said laser passage of said lower housing; and
    alignment means for aligning said lens plate means to said laser passage in said upper housing and to said laser passage in said lower housing.

6. The system of claim 5 wherein said adapter coupling assembly comprising an extended portion having external threads.

7. The system of claim 5 wherein said lens exchanging means comprising a slot in said lower housing and a thumb screw coupled to said lens plate means passing through said slot such that a circumferential force on said thumb screw causes said lens plate means to rotate thereby changing from said first lens position to said second lens position.

8. The system of claim 5 wherein said alignment means comprising a threaded hole in the center of said upper housing, a conical recess in said lens plate means, and a set screw with conical tip that is screwed into said threaded hole until said conical tip of said set screw presses into said conical recess in said lens plate means thereby aligning said lens plate means to a correct position relative to said upper housing and to said lower housing.

9. The system of claim 1 wherein said surgical tool means is a laparoscope.

10. A laser surgical system comprising, in combination:
    a laser housing;
    laser cutting means for cutting tissue during surgery enclosed in a laser housing;
    laser aiming means coupled to said laser cutting means for aiming said laser cutting means and enclosed in said laser housing with said laser cutting means;
    coupler means coupled to said laser housing to position and focus said laser cutting means and said laser aiming menas;
    lens exchanger apparatus coupled to said coupler menas; and
    surgical tool means coupled to said lens exchanger apparats, said lens exchanger apparatus comprises, in combination:
    an upper housing having a laser passage and an adapter coupling assembly;
    a lower housing having a laser passage coincident to said laser passage of said upper housing, said lower housing being fixedly coupled to said upper housing;
    lens plate means located within said lower housing for providing multiple lenses, one of which aligns with said laser passage in said upper housing and with said laser passage in said lower housing in a first lens position;
    lens exchanging means for moving the position of said one of said multiple lenses from said first lens position to a second lens position to align a different lens of said multiple lenses with said laser passage of said upper housing and with said laser passage of said lower housing; and
    alignment means for aligning said lens plate menas to said laser passage in said upper housing and to said laser passage in said lower housing, 11. A method for exchanging lenses in a laser surgical system during surgery comprising the steps of:
    providing a laser housing;
    providing laser cutting means consisting of a single laser cutting beam for cutting tissue during surgery enclosed in a laser housing;
    providing laser aiming menas coupled to said laser cutting means for aiming said laser cutting means and enclosed in said laser housing with said laser cutting means;
    providing coupler menas having a fixed lens assembly located therein and coupled to said laser housing to position and focus said laser cutting means and said laser aiming menas;
    providing lens exchanger apparatus means comprising a single rotatable plate coupled to said coupler means for selectively rotating lenses to permit continued operation of the laser surgical system during surgery, said lenses being removably coupled to said single rotatable plate; and providing surgical tool means coupled to said lens exchanger means.

12. The method of claim 11 wherein said laser cutting means comprising an invisible, relatively high power Carbon Dioxide ($CO_2$) laser.

13. The method of claim 11 wherein said laser aiming means comprising a visible, relatively low power Helium Neon (HeNe) laser.

14. The method of claim 11 wherein said coupler menas comprising connection means which couples said laser housing to said coupler means, and lens assembly means for focusing the laser output of said laser cutting means and said laser aiming means.

15. The method of claim 11 wherein providing said lens exchanger apparatus means comprises the steps of:

providing an upper housing having a laser passage and an adapter coupling assembly;

providing a lower housing having a laser passage coincident to said laser passage of said upper housing said lower housing being fixedly coupled to said upper housing;

providing lens plate means located within said lower housing for providing multiple lenses, one of which aligns with said laser passage in said upper housing and with said laser passage in said lower housing in a first lens position;

providing lens exchanging menas for moving the position of said one of said multiple lenses from said first lens position to a second lens position to align a different lens of said multiple lenses with said laser passage of said upper housing and with said laser passage of said lower passage; and providing alignment means for aligning said lens plate means to said laser passage in said upper housing and to said laser passage in said lower housing.

16. The method of claim 15 wherein providing said adapter coupling assembly comprises the step of providing an extended portion having external threads.

17. The method of claim 15 wherein providing surgical tool coupling means comprises the step of providing an extended portion having internal threads.

18. The method of claim 15 wherein providing said lens exchanging means comprises the step of providing a slot in said lower housing and a thumb screw coupled to said lens plate means passing through said slot such that a circumferential force on said thumb screw causes said lens plate means to rotate thereby changing from said first lens position to said second lens position.

19. The method of claim 15 wherein providing said alignment menas comprises the step of providing a threaded hole in the center of said upper housing, providing a conical recess in said lens plate menas, and providing a set screw with conical tip that is screwed into said threaded hole until said conical tip of said set screw presses into said conical recess in said lens plate means thereby aligning said lens plate menas to a correct position relative to said upper housing and to said lower housing.

20. The method of claim 15 further comprising the steps of:

placing said lens plate means in said first lens position;
performing surgery as required;
placing said lens plate means in said second lens position as required by the surgeon.

21. The method of claim 11 wherein providing said surgical tool means comprises the step of providing a laparoscope.

* * * * *

UNITED STATES PATENT AND TRADEMARK OFFICE
CERTIFICATE OF CORRECTION

PATENT NO. : 5,312,397
DATED : May 17, 1994
INVENTOR(S) : Ioan Cosmescu

It is certified that error appears in the above-indentified patent and that said Letters Patent is hereby corrected as shown below:

Col. 6, line 57
Claim 11, line 7, change "menas" to --means--.
Col. 6, line 61
Claim 11, line 11, change "menas" to --means--.
Col. 6, line 64
Claim 11, line 14, change "menas" to --means--.
Col. 7, line 31
Claim 15, line 14, change "menas" to --means--.
Col. 8, line 18
Claim 19, line 2, change "menas" to --means--.
Col. 8, line 20
Claim 19, line 4, change "menas" to --means--.
Col. 8, line 24
Claim 19, line 8, change "menas" to --means--.

Signed and Sealed this

Sixteenth Day of August, 1994

Attest:

BRUCE LEHMAN

*Attesting Officer*          *Commissioner of Patents and Trademarks*